United States Patent [19]
Warburton

[11] Patent Number: 5,154,487
[45] Date of Patent: Oct. 13, 1992

[54] SUPPORT APPARATUS FOR A TORSO

[76] Inventor: Patricia G. Warburton, 9289 W. Baltic Dr., Lakewood, Colo. 80227

[21] Appl. No.: 752,762

[22] Filed: Aug. 30, 1991

[51] Int. Cl.⁵ .............................................. A47C 31/00
[52] U.S. Cl. .................................. 297/465; 297/484; 297/485; 128/874
[58] Field of Search ............... 297/465, 484, 485, 464; 128/869, 870, 873, 874, 875, 876

[56] References Cited

U.S. PATENT DOCUMENTS

| | | | |
|---|---|---|---|
| 2,170,703 | 8/1939 | Waxman et al. | 128/874 X |
| 2,851,033 | 9/1958 | Posey | 297/485 X |
| 3,136,311 | 6/1964 | Lewis | 128/134 |
| 3,827,716 | 8/1974 | Vaughn et al. | 280/150 |
| 4,117,840 | 10/1978 | Rasure | 128/874 |
| 4,224,474 | 10/1980 | Rupert et al. | 297/484 |
| 4,330,152 | 5/1982 | Legan et al. | 297/465 |
| 4,541,425 | 9/1985 | Yetter, Jr. | 128/134 |
| 4,568,125 | 2/1986 | Sckolnik | 297/467 |
| 4,608,973 | 9/1986 | Green et al. | 128/874 |
| 4,753,482 | 6/1988 | Warren | 297/458 |
| 4,854,638 | 8/1989 | Marcus et al. | 297/250 |
| 4,979,779 | 12/1990 | Williams | 297/484 X |

Primary Examiner—Peter R. Brown
Attorney, Agent, or Firm—Sheridan, Ross & McIntosh

[57] ABSTRACT

A portable, customizable support apparatus for a patient's torso is provided for maintaining the patient in a substantially upright sitting position. The apparatus includes a left side member, a right side member and a back member and assemblies for securing the apparatus to the patient and to a seating unit. The support apparatus also includes a device for interconnecting the left and right side members at the front of the torso such that the left and right side members and back member substantially surround the patient's torso. The assembled apparatus can be used with most conventional chairs and seats, including geriatric chairs and wheelchairs. A method of providing support for a patient in a substantially upright sitting position is also provided which includes the steps of measuring certain dimensions of the patient, selecting appropriately sized members, securing the members together using interconnect devices, securing the apparatus about the patient's torso and securing the apparatus to a seating unit.

14 Claims, 3 Drawing Sheets

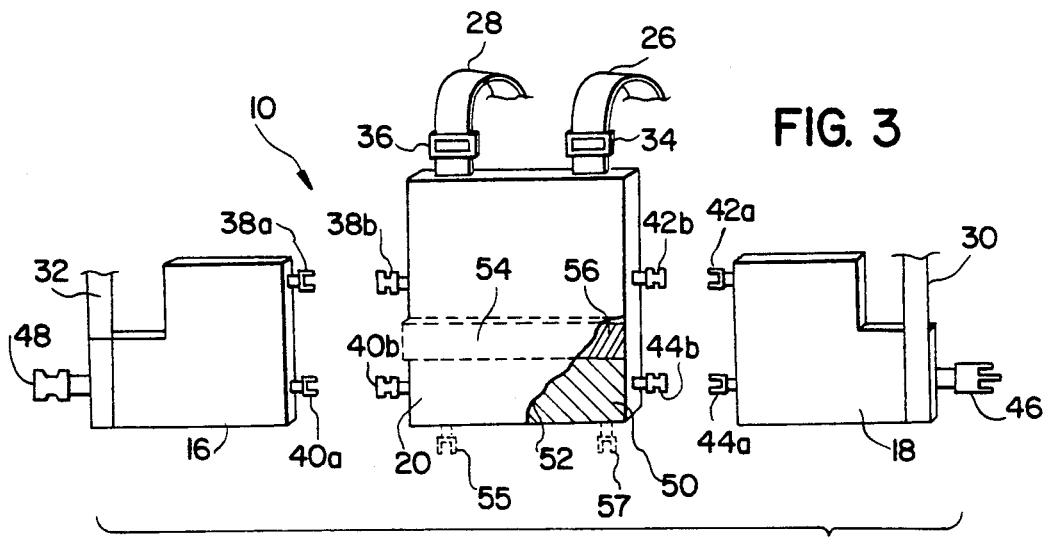
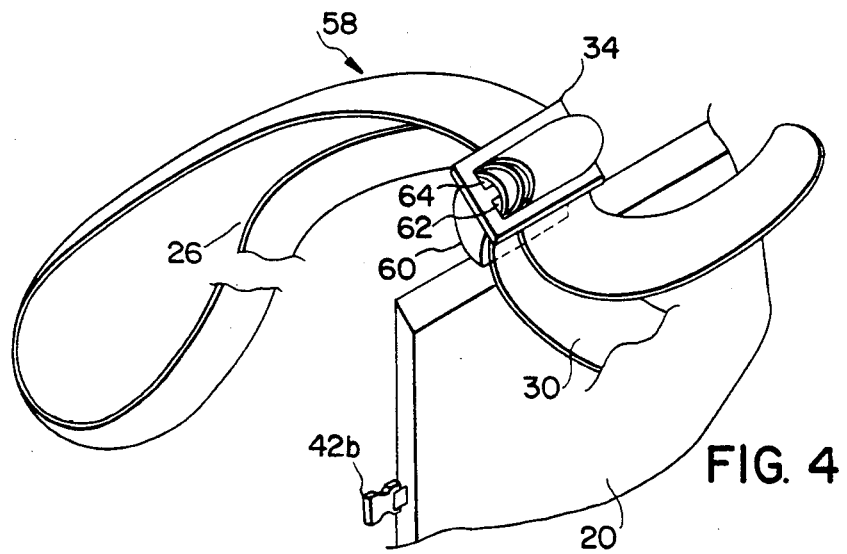
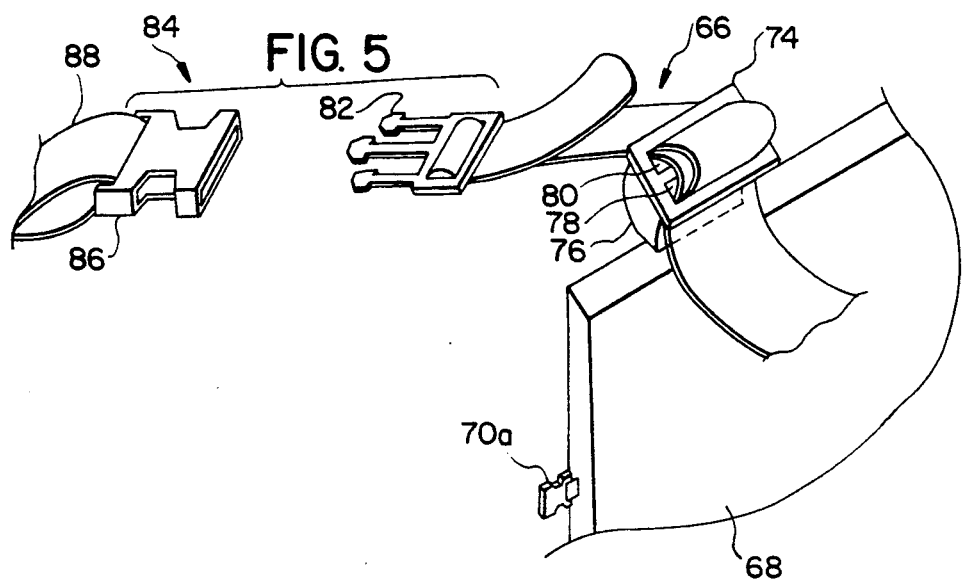

SUPPORT APPARATUS FOR A TORSO

This application relates to U.S. patent application Ser. No. 07/682,634, filed Apr. 9, 1991.

FIELD OF THE INVENTION

The present invention relates to a device for supporting a person in a substantially upright sitting position, and particularly to a portable, customizable support apparatus for a torso.

BACKGROUND OF THE INVENTION

In connection with the support of patients to enable them to sit upright in a chair or other seating unit, a variety of support devices have been proposed. The need for devices for maintaining patients in a sitting position is particularly acute for those patients whose own muscles provide insufficient support, such as paraplegic patients and those with weak torso muscles. In such patients, the body's normal nervous or muscle systems have been injured, impaired or weakened to such an extent that they do not allow the torso to remain in an upright position, such as in a chair. These patients tend to slump down, lean forward or tilt toward the side. Even when in a geriatric chair, with its high back and tilted seat and back, a paraplegic may not remain in position. Often patients are secured to a chair with a single waist belt. Some may, however, lean so far forward that their head rests on their knees and their chair tips forward, presenting a significant risk of severe injury. Consequently, many patients require external support to compensate for the body's weakened or damaged internal support.

Many devices that have been proposed are positioned on or about the patient and secured to the chair or seating unit. For example, one such device is disclosed in U.S. Pat. No. 2,851,033 by Posey. Posey discloses an apron-like device for securing a person to a chair. The one-piece device wraps around the front of the person and is attached to the sides and seat of the chair with hip, abdomen, chest and shoulder straps to hold the patient in the chair. U.S. Pat. No. 4,330,152 by Legan et al. discloses another apron-like device for securing a person in a chair. The one-piece device includes shoulder straps which cooperate with waste loops for attaching the device to a chair and for holding the patient in the chair. U.S. Pat. No. 3,136,311 by Lewis discloses a vest-like device for securing a person to a chair. The one-piece device wraps around the person and is attached to the back of the chair with straps to hold the patient in the chair. None of the foregoing devices includes detachable, custom fitted, flexible cushions having a desired thickness for support.

U.S. Pat. No. 4,541,425 by Yetter Jr. discloses a restraining device having a head band secured about the user's head and attached by a strap to the back of a chair. It also includes two elongated side cushions positioned vertically between the chair arms and the user. It does not include a back cushion and does not wrap around the person to provide support for the torso.

Despite a variety of support systems for paraplegics and other people having problems maintaining their torso in a sitting position, it would be advantageous to provide an apparatus that substitutes for the body's own support system, provides comfort, is portable and easy to use and can be customized to fit each individual patient.

SUMMARY OF THE INVENTION

In accordance with the present invention, a portable apparatus is provided for supporting a person's torso in a substantially upright position in a seating unit. The apparatus includes a back member, a flexible left side member interconnected with the back member, a flexible right side member interconnected with the back member, a device for interconnecting the left and right side members at the front of the torso and an assembly for securing the apparatus to a seating unit. The securing assembly includes back straps having one end interconnected to the top of the back member and an opposite end for securing to the back of the seating unit. The securing assembly also includes shoulder straps disposed between the front of each side member and the top of the back member where they are, preferably, interconnected with the back straps.

The widths of the left and right side members are selected such that, when the back and shoulder straps are properly adjusted and the left and right side members interconnected at the front of the torso, the apparatus fits snugly and substantially completely around the patient's torso. The height of each side member can also be selected to fit each patient. Thus, the apparatus can be customized to fit each patient and permits the patient's torso to be fully supported in an upright position so that the patient remains in the seating unit and does not slide down, slump forward or lean sideways. In conjunction with the seating unit, therefore, the apparatus provides a substitute for the patient's impaired muscles.

The torso support apparatus of the present invention is lightweight and portable, making it easy to move from one chair or location to another as the patient moves and is customizable to accommodate substantially all patients and achieve the desired support and comfort in a variety of seating units, including wheelchairs and geriatric chairs. The apparatus is also easily assembled using the three interchangeable pieces and associated interconnecting devices.

BRIEF DESCRIPTION OF THE DRAWINGS

For a more complete understanding of the present invention, and the advantages thereof, reference is now made to the following description taken in conjunction with the accompanying drawings, in which:

FIG. 3 illustrates the separate members of the present invention, with the back member partially cut away;

FIG. 4 is a perspective view of a portion of the back member and one embodiment of an interconnecting strap;

FIG. 5 is a perspective view of a portion of the back member and an alternative embodiment of an interconnecting strap.

DETAILED DESCRIPTION

The present invention is best understood by referring to FIGS. 1–6 of the drawings, like numerals being used for like and corresponding parts of the various drawings.

Figure 1:
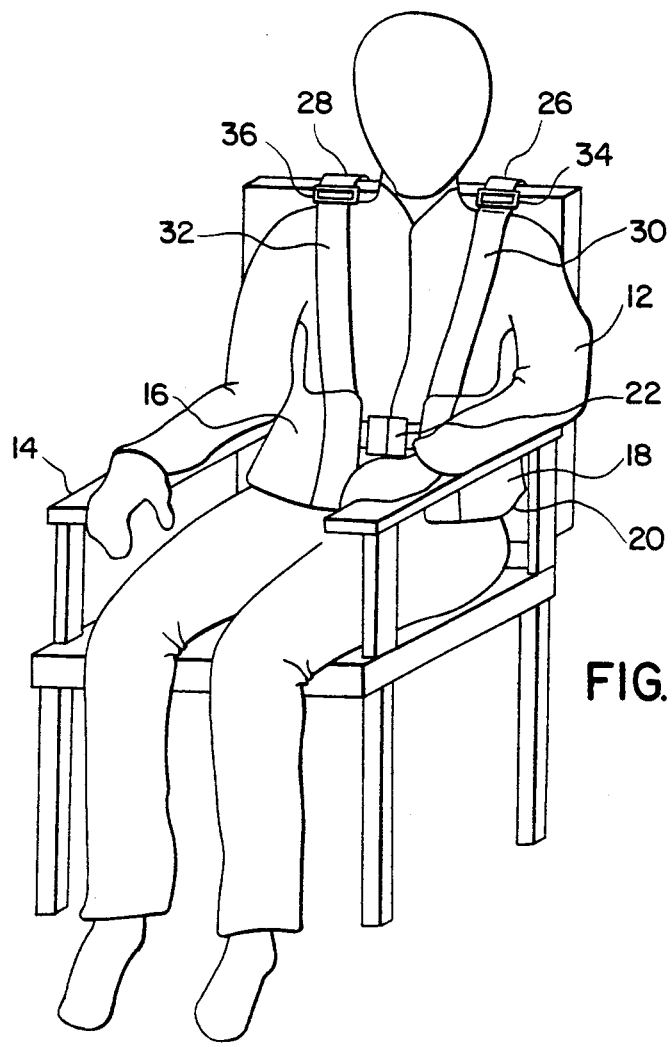
FIG. 1 illustrates the use of the present invention by a patient in a chair, as viewed from the front.
Figure 2:
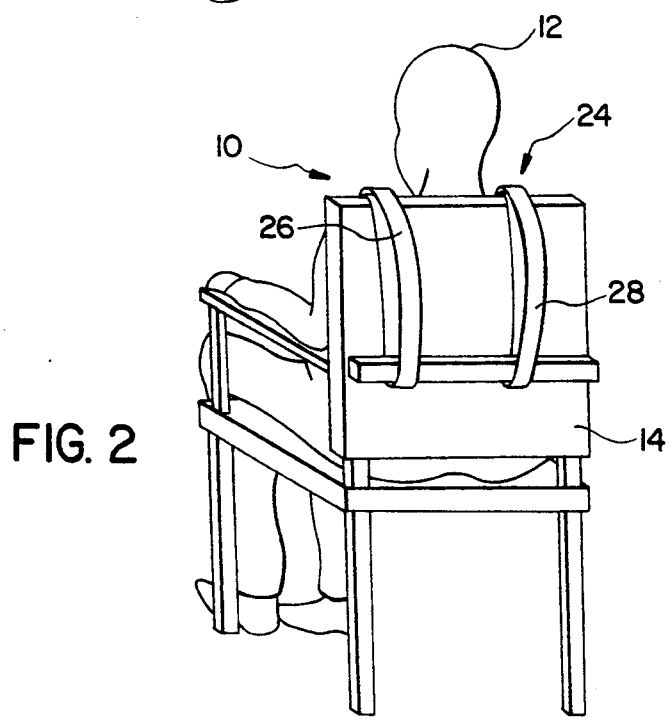
FIG. 2 illustrates the use of the present invention by a patient in a chair, as viewed from the back.
Figure 6A:
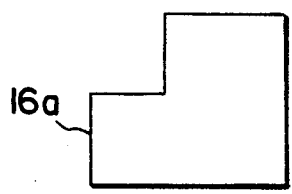
FIGS. 6a–6m illustrate a plurality of differently dimensioned members from which appropriate members are selected for a particular patient.
Figure 6G:
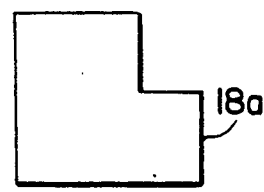
Figure 6B:
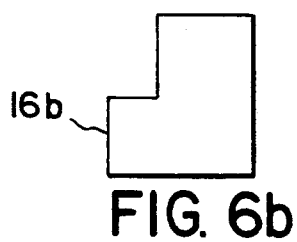
Figure 6H:
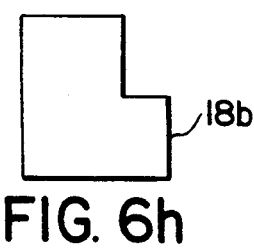
Figure 6C:
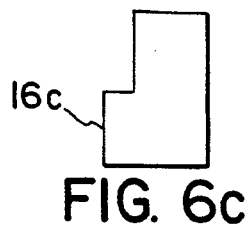
Figure 6I:
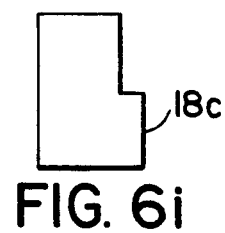
Figure 6D:
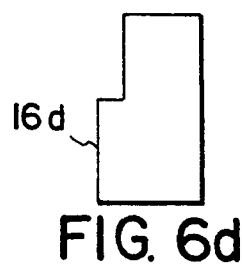
Figure 6M:
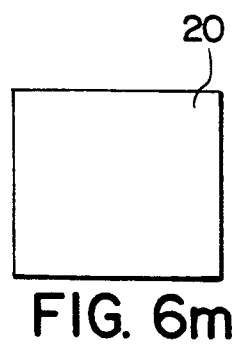
Figure 6J:
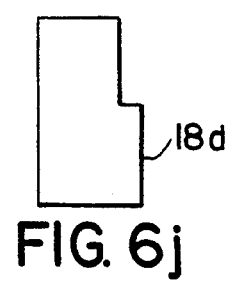
Figure 6E:
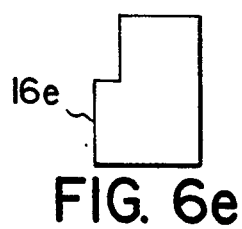
Figure 6K:
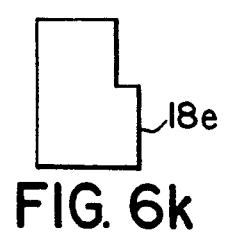
Figure 6F:
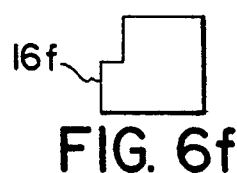
Figure 6L:
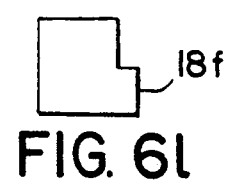

FIGS. 1 and 2 illustrate the use of a torso support apparatus 10 of the present invention by a patient 12 in a chair, such as a geriatric chair 14. Apparatus 10 includes a flexible, L-shaped right side member or cushion 16, a flexible, L-shaped left side member or cushion 18 and a back member or cushion 20. Apparatus 10 also includes an interconnect device 22 for interconnecting right and left side members 16 and 18 at the front of the torso of patient 10. Apparatus 10 also includes an assembly 24 for securing apparatus 10 to chair 14.

Securing assembly 24 includes left and right back straps 26 and 28 and left and right shoulder straps 30 and 32. One end of left shoulder strap 30 is secured, such as by sewing, to a front portion of left side member 18 and the other end is interconnected with back member 20 at the top thereof near the upper left corner with a left adjustable fastener 34. Similarly, one end of right shoulder strap 32 is secured to a front portion of right side member 16 and the other end is interconnected with back member 20 at the top thereof near the upper right corner with a right adjustable fastener 36. Because apparatus 10 supports much of the patient's body weight, it is preferable that shoulder straps 30 and 32 be sewn at least to both the top and bottom of the front portion of side members 18 and 16, as shown in FIG. 3, to reduce the risk that shoulder straps 30 and 32 will separate from side members 18 and 16. Left back strap 26 is interconnected with back member 20 at the top thereof near the left side. Similarly, right back strap 28 is interconnected with back member 20 at the top thereof near the right side. Preferably, left back strap 26 is a continuation of, or integral with, left shoulder strap 30 and right back strap 28 is a continuation of, or integral with, right shoulder strap 32. As will be discussed in more detail with respect to FIG. 4, fasteners 34 and 36 can be luer locks secured to the top of back member 20 with the straps passing through two slots in the fasteners.

Referring still to FIG. 3, right side member 16 and back member 20 are interconnected by detachable side release buckles, comprising male (or female) clips 38a and 40a on right side member 16 which cooperate with female (or male) clips 38b and 40b on back member 20. Similarly, left side member 18 and back member 20 are interconnected by detachable side release buckles, comprising male (or female) clips 42a and 44a on left side member 18 which cooperate with female (or male) clips 42b and 44b on back member 20. Interconnect device 22 for interconnecting the front portions of right and left side members 16 and 18 preferably includes an adjustable front buckle having a male portion 46 secured by a strap to one of right or left side members 16 and 18 which cooperates with a female portion 48 secured with a strap to the other of right and left side members 16 and 18.

Right and left side members 16 and 18 and back member 20 preferably include lightweight, flexible cushion material, such as foam 50 in back member 20, covered with conventional covering material, such as covering 52. Covering 52 is, preferably, lightweight, water resistant and washable, such as Naugahyde. Back member 20 also preferably includes a lumbar support section 54 which can include an additional thickness 56 of foam. The foam employed for lumbar support section 54 can also have a higher density than foam 50 used for the balance of back member 20, thereby providing firmer support and comfort for patient 12.

If desired, additional side release buckles 55 and 57 (shown in phantom) can be provided for interconnecting back member 20 to a separate seat member or cushion, thus providing additional comfort for patient 12.

FIG. 4 is a view of a top portion of back member 20 and portions of left back and shoulder straps 26 and 30 in more detail. For ease of construction and use, left back and shoulder straps 26 and 30 are preferably portions of a single, flexible strap 58, one end of which is secured to left side member 18 (in the manner illustrated in FIG. 3). Fastener 34 is secured to back member 20 by a short strap 60 sewn to the top of back member 20 near the upper left corner. The free end of strap 58 passes through two parallel slots 62 and 64 in fastener 34 and passes around an appropriate part of the frame of seating unit 14. The free end then passes back through slots 64 and 62 to secure strap 58 to fastener 34. A similar arrangement is employed on the right side of back member 20.

FIG. 5 illustrates an alternative arrangement for securing a strap 66 to a back member 68. Side release buckle clips 70a and 72a cooperate with corresponding clips on a left side member for interconnecting back member 68 with the left side member. Similar clips are attached to the right side of back member 68 for interconnecting back member 68 with a right side member. One end of strap 66 is secured to a front portion of the left side member. A luer lock fastener 74 is secured to back member 68 by a short strap 76 sewn to the top of back member 68. The free end of strap 66 passes through two slots 78 and 80 in fastener 74 and then passes through a slot in a male (or female) portion 82 of a buckle 84. The free end of strap 66 then passes back through slots 80 and 78 to secure straps 66 to fastener 74. A female (or male) portion 86 is secured to another strap 88 which is secured to an appropriate location on a seating unit. A similar arrangement is employed on the right side of back member 68. In use, male and female portions 82 and 86 of buckle 84, and corresponding portions of a buckle on the right side of back member 68, are interconnected with each other to secure the torso support apparatus to the seating unit. Strap 88 (and the corresponding strap on the right side) can be secured, temporarily or permanently, to the back of the seating unit. Similar straps can also be secured to other seating units frequently used by the patient, thus, making it convenient for the patient to be moved to different seating units.

Referring again to FIGS. 1-3, to use the apparatus of the present invention, the arms of patient 12 are placed through the openings formed by left and right shoulder straps 30 and 32 in a manner similar to putting on a vest. Front buckle portions 46 and 48 are interconnected and tightened such that right and left side members 16 and 18 and back member 20 substantially and snugly surround patient 12. Left and right shoulder straps 30 and 32 are also tightened at left and right adjustable fasteners 34 and 36. For increased comfort and support, the bottom of each side member 16 and 18 should rest upon the patient's iliac crest at the top of the patient's pelvis and the top of each side member 16 and 18 should be about three inches below the patient's axilla. Thus, the torso of patient 12 is firmly, securely and comfortably supported.

Patient 12 is placed in a sitting position in chair 1 and left and right back straps 26 and 28 are secured to the back of chair 14, or interconnected with straps previously secured to chair 14 (as detailed in conjunction with FIG. 5). Left and right back straps 26 and 28 are then tightened, enabling patient 12 to be securely supported in a substantially upright position in chair 14. A paraplegic patient may remain primarily in a specialized seating unit, such as geriatric chair 14 having a back which is higher than the patient's back and having a tilted seat and back. For a patient in such a chair, back straps 26 and 28 are pulled up and over the back of the chair and secured thereto. Consequently, the patient's torso, substantially surrounded by apparatus 10, is subjected to a lifting and stabilizing force by back straps 26 and 28. The lifting force is substantially uniformly distributed around the torso by apparatus 10 and substantially maintains the muscles of the torso, such as the left and right oblique muscles, in a uniform state of extension/contraction, thus reducing tilt, lean and slumping.

For patients whose torso muscles are weak, but not paralyzed, apparatus 10 can be used in conjunction with various types of conventional seating units and wheelchairs having lower backs, including table chairs, sofas and automobile seats. Back straps 26 and 28 can be secured at appropriate locations at the back of the seating unit to permit patient 12 to remain in a substantially upright sitting position and be held firmly against the back o the seating unit. Other arrangements of securing straps can be employed when the back of a seating unit does not have convenient locations for securing back straps 26 and 28. For example, back straps 26 and 28 can be secured to the top of the back legs of a chair or, when patient 12 is to be seated in the front seat of an automobile, back straps 26 and 28 can be secured to a seat belt in the back seat.

FIGS. 6a-6m illustrate an embodiment of support apparatus 10 of the present invention in which several different right side members 16a-16f and several different left side members 18a-18f, along with back member 20, are available to be selected and assembled for a particular patient. Right side members 16a-16c differ in width from each other; similarly, left side members 18a-18c differ in width from each other. Right side members 16d-16f differ in height from each other; similarly, left side members 18d-18f differ in height from each other. It will be appreciated that more or fewer sizes of each member of support apparatus 10 can be made available, including different sizes of back member 20. Additionally, specially dimensioned and manufactured members can also be provided for a patient with special needs.

A practitioner, such as an occupational therapist, is trained to evaluate a patient and select and assemble appropriately dimensioned or configured members. Such training preferably includes learning how to perform a neurological evaluation, how to measure a patient, how to apply the measurements and evaluation to the selection of properly sized members of support apparatus 10, and how to assemble the members into a complete apparatus. The practitioner also learns whether an assembled support apparatus provides the proper support for a particular patient and, if not, how to replace one or more of the members to assure a proper fit.

Measurements taken by the practitioner include the girth of the patient's torso and the length of the torso length from the patient's iliac crest to the axilla. Based upon these measurements, the practitioner selects left and right side members having a height equal to about three inches less than the torso length and having a width such that the assembled apparatus will substantially surround the patient's torso.

Once the patient has been measured and fully evaluated and the practitioner has selected appropriate members, the support apparatus is assembled. The members are interconnected with the detachable side release buckles and assembled support apparatus 10 is placed on patient 12. As previously described, the lengths of the various straps are adjusted to provide a secure fit, patient 12 is positioned in chair 14, and support apparatus is secured thereto. Once properly adjusted and secured to chair 14, apparatus 10 need not be removed or readjusted. Instead, it can remain secured to chair 14 and removed from patient 12. To use again, patient 12 is positioned in chair 14 and apparatus 10 placed on and secured around patient 12 as previously described.

Based on the foregoing description, a number of important features of the present invention are readily discerned. A support apparatus for a patient's torso is provided to be used with a variety of conventional separate seating units, such as a geriatric chair or a wheelchair. The support apparatus is portable so that it is easily carried. It can be adapted to different conventional seating units and can be customized for a particular patient by having a number of different sized members from which appropriately dimensioned members for the particular patient can be selected. In selecting the appropriate members, it is preferred that measurements be taken of particular body dimensions of the patient. Each of the members is easily assembled/disassembled from other members. The side and back members are also constructed to enhance patient support and comfort. Thus, the torso support apparatus of the present invention, in combination with a seating unit, can substitute for the patient's own internal support system when that system fails, for any of a number of reasons, to provide the support necessary to maintain the patient in a substantially upright position.

The foregoing description of the invention has been presented for purposes of illustration and description. The description is not intended to limit the invention to the form disclosed. Consequently, variations and modifications commensurate with the above teachings and the skill or acknowledge in the relevant art are within the scope of the present invention. The preferred embodiments described herein above are further intended to explain the best mode known of practicing the invention and to enable others skilled in the art to utilize the invention in various embodiments and with the various modifications required by their particular applications or uses of the invention. It is intended that the appended claims be construed to include alternative embodiments to the extent permitted by the prior art.

What is claimed is:

1. A support apparatus for a torso, comprising:
a back member for contacting the back of a person;
a flexible left side member interconnected with said back member;
a flexible right side member interconnected with said back member;
first means for interconnecting said left and right side members at the front of the torso, wherein said back member, said left side member and said right side member substantially surround the torso of the person; and
second means for securing the apparatus to a seating means, said second means including:
a first flexible strap having:
a first segment secured to a front portion of said right side member;

a second segment securable to said seating means; and a third segment, between said first and second segments, adjustably interconnected to a first portion of said back member; and a second flexible strap having:

a first segment secured to a front portion of said left side member;

a second segment securable to said seating means;

a third segment, between said first and second segments, adjustably interconnected to a second portion of said back member;

third means for adjustably interconnecting said third segment of said first strap to said first portion of said back member, said third means including a first fastener for slidably receiving said third segment of said first strap; and fourth means for adjustably interconnecting said third segment of second strap to said second portion of said back member, said fourth means including a second fastener for slidably receiving said third segment of said second strap.

2. An apparatus, as claimed in claim 1, wherein:

said second segment of said first strap includes a first buckle portion engagable with a second buckle portion securable to said seating means; and said second segment of said second strap includes a third buckle portion engagable with a fourth buckle portion securable to said seating means.

3. An apparatus, as claimed in claim 1, wherein said second means includes:

fifth means for securing said back member to said seating means.

4. An apparatus, as claimed in claim 3, wherein said fifth means includes:

a first flexible strap having a first end secured to a first portion of said back member and a second end for securing to said seating means; and a second flexible strap having a first end secured to a second portion of said back member and a second end for securing to said seating means.

5. An apparatus, as claimed in claim 4, wherein said fifth means further includes:

means for adjusting the lengths of said first and second straps.

6. An apparatus, as claimed in claim 5, wherein said second means further includes:

sixth means for supporting the person in a substantially upright position.

7. An apparatus, as claimed in claim 6, wherein said sixth means includes:

a third flexible strap having a first end secured to a front portion of said right side member and a second end interconnected with said first strap proximate to said first portion of said back member; and a fourth flexible strap having a first end secured to a front portion of said left side member and a second end interconnected with said second strap proximate to said second portion of said back member.

8. An apparatus, as claimed in claim 7, wherein said sixth means further includes:

means for adjusting the lengths of said third and fourth straps.

9. An apparatus, as claimed in claim 1, wherein:

the combined widths of said right side member, said left side member and said back member is approximately equal to the girth of the torso.

10. An apparatus, as claimed in claim 1, wherein:

The height of each of said right and left side members is approximately three inches less than the distance from the person's iliac crest to the person's axilla.

11. An apparatus, as claimed in claim 1, wherein:

said right member and said left side member each have an L shape.

12. An apparatus, as claimed in claim 1, wherein:

said back member, said right side member and said left side member each comprise a flexible foam material.

13. An apparatus, as claimed in claim 1, wherein:

said back member includes a lumbar support.

14. A support apparatus for a torso, comprising:

a back member for contacting the back of a person;

a flexible left side member interconnected with said back member;

a flexible right side member interconnected with said back member;

first means for interconnecting said left and right side members at the front of the torso, wherein said back member, said left side member and said right side member substantially surround the torso of the person;

second means for securing the apparatus to a seating means;

a first set of side release buckles for detachably interconnecting said right side member with said back member; and a second set of side release buckles for detachably interconnecting said left side member with said back member.

* * * * *